United States Patent
Wu et al.

(10) Patent No.: US 11,236,112 B2
(45) Date of Patent: Feb. 1, 2022

(54) CRYSTAL FORM AND SALT FORM OF TGF-βRI INHIBITOR AND PREPARATION METHOD THEREFOR

(71) Applicant: GENFLEET THERAPEUTICS (SHANGHAI) INC., Shanghai (CN)

(72) Inventors: Lifang Wu, Shanghai (CN); Huijun He, Shanghai (CN); Jianyu Lu, Shanghai (CN); Charles Z. Ding, Shanghai (CN); Lihong Hu, Shanghai (CN); Weidong Li, Shanghai (CN); Shenyi Shi, Shanghai (CN); Jian Li, Shanghai (CN); Shuhui Chen, Shanghai (CN)

(73) Assignee: GENFLEET THERAPEUTICS (SHANGHAI) INC., Shanghai (CN)

( * ) Notice: Subject to any disclaimer, the term of this patent is extended or adjusted under 35 U.S.C. 154(b) by 0 days.

(21) Appl. No.: 16/771,977

(22) PCT Filed: Dec. 13, 2018

(86) PCT No.: PCT/CN2018/120905
§ 371 (c)(1),
(2) Date: Jun. 11, 2020

(87) PCT Pub. No.: WO2019/114792
PCT Pub. Date: Jun. 20, 2019

(65) Prior Publication Data
US 2021/0079021 A1 Mar. 18, 2021

(30) Foreign Application Priority Data
Dec. 13, 2017 (CN) .......................... 201711331447.7

(51) Int. Cl.
| C07D 519/00 | (2006.01) |
| A61P 35/00 | (2006.01) |
| A61K 31/444 | (2006.01) |
| A61K 31/416 | (2006.01) |
| A61K 31/4439 | (2006.01) |
| C07D 487/04 | (2006.01) |
| C07D 471/04 | (2006.01) |

(52) U.S. Cl.
CPC ........ *C07D 519/00* (2013.01); *C07B 2200/13* (2013.01)

(58) Field of Classification Search
CPC .. C07D 519/00; C07D 487/04; C07D 471/04; C07D 401/14; C07B 2200/13; A61P 35/00; A61K 31/444; A61K 31/416; A61K 31/4439
See application file for complete search history.

(56) References Cited

U.S. PATENT DOCUMENTS

| 3,038,004 A * | 6/1962 | Copp .................... C07C 215/28 562/84 |
| 6,489,343 B2 * | 12/2002 | Pineiro ................... A61P 25/00 514/326 |
| 6,958,354 B2 | 10/2005 | Munchhof et al. |
| 7,087,626 B2 | 8/2006 | Beight et al. |
| 8,039,639 B2 | 10/2011 | Groneberg et al. |
| 10,548,883 B2 | 2/2020 | Sun et al. |
| 2004/0116474 A1 | 6/2004 | Munchhof et al. |
| 2013/0005980 A1 * | 1/2013 | Jaryal .................. C07D 213/81 546/291 |
| 2019/0151299 A1 | 5/2019 | Sun et al. |

FOREIGN PATENT DOCUMENTS

| CN | 201711331447.7 | 11/2002 |
| CN | 1511157 A | 7/2004 |
| CN | 1681501 A | 10/2005 |
| EA | 200500377 A1 | 8/2005 |
| EA | 007782 B1 | 2/2020 |
| EP | 3470409 A1 | 12/2017 |
| JP | 2019518066 A | 6/2019 |
| RU | 2442777 C2 | 2/2012 |
| RU | 2018146264 A3 | 7/2020 |

(Continued)

OTHER PUBLICATIONS

Stahl, P.H., Handbook of Pharmaceutical salts properties, selection, and use. John Wiley & Sons, 2008, Ch 12:265-327.*
Neau, S. H., "Pharmaceutical salts." Water-Insoluble Drug Formulation, Second Edition. Ed. Rong Liu. CRC Press, 2008. 417-435.*
Bastin, R.J., "Salt selection and optimisation procedures for pharmaceutical new chemical entities." Organic Process Research & Development 4.5 (2000): 427-435.*
Morris, K.R.,"An integrated approach to the selection of optimal salt form for a new drug candidate." International journal of pharmaceutics 105.3 (1994): 209-217.*

(Continued)

*Primary Examiner* — John M Mauro
(74) *Attorney, Agent, or Firm* — Harness, Dickey & Pierce, P.L.C.

(57) ABSTRACT

Disclosed in the present invention are a crystal form and salt form of a TGF-βR1 inhibitor and a preparation method therefor, and further disclosed is an application of the crystal form and the salt form in preparation of medicines for treating cancers.

(I)

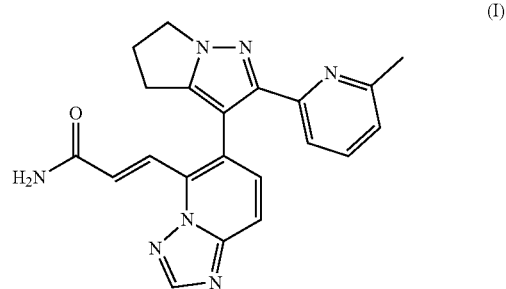

16 Claims, 4 Drawing Sheets

(56) References Cited

FOREIGN PATENT DOCUMENTS

| WO | WO-02094833 A1 | 11/2002 |
| WO | WO-2004050659 A1 | 6/2004 |
| WO | WO-2016160881 A1 | 10/2016 |
| WO | WO-2017215506 A1 | 12/2017 |

OTHER PUBLICATIONS

Badawy, S.I.,"Salt selection for pharmaceutical compounds." Preformulation in Solid Dosage Form Development (Informa Healthcare, 2008) Chapter 2.3, (2008): 63-80.*

Gould, P.L., "Salt selection for basic drugs." International Journal of Pharmaceutics 33.1 (1986): 201-217.*

Serajuddin, A.T.M., "Salt formation to improve drug solubility." Advanced drug delivery reviews 59.7 (2007): 603-616.*

Swarbrick, J., "Salt Forms of Drugs and Absorption." Encyclopedia of Pharmaceutical Technology 13 (1988): 453-499.*

Pfizer, Inc, v. Apotex, 480 F.3d 1348, *; 2007 U.S. App. Lexis 6623, **; 82 U.S.P.Q.2D (BNA) 1321: p. 1-13.*

Herbertz, S., "Clinical development of galunisertib (LY2157299 monohydrate), a small molecule inhibitor of transforming growth factor-beta signaling pathway." Drug design, development and therapy 9 (2015): 4479-4499.*

Hanks, B.A., "Combinatorial TGF-β signaling blockade and anti-CTLA-4 antibody immunotherapy in a murine BRAFV600E-PTEN-/-transgenic model of melanoma." (2014): 3011-3011.*

Dec. 21, 2020 Russian Office Action issued in Russian Patent Application No. 2020121754/04(037350).

Extended European Search Report issued in European Patent Application No. 18888487.8, dated Mar. 26, 2021.

Chinese First Office Action issued in Chinese Patent Application No. 2018800801699, dated Apr. 13, 2021.

Sep. 16, 2020 Australian Office Action issued in Australian Patent Application No. 2018383853.

Nov. 2, 2019 International Search Report issued in International Patent Application No. PCT/CN2018/120905.

Nov. 2, 2019 Written Opinion of the International Searching Authority issued in International Patent Application No. PCT/CN2018/120905.

Jul. 13, 2021 Japanese First Office Action issued in Japanese Patent Application No. 2020-532602.

Nov. 2, 2021 Canadian First Office Action issued in Canadian Patent Application No. 3,085,498.

Oct. 26, 2021 Japanese Second Office Action issued in Japanese Patent Application No. 2020-532602.

* cited by examiner

CRYSTAL FORM AND SALT FORM OF TGF-βRI INHIBITOR AND PREPARATION METHOD THEREFOR

CROSS-REFERENCE TO RELATED APPLICATIONS

This application is a 371 National Phase of International Application No. PCT/CN2018/120905, filed Dec. 13, 2018, which claims the benefit of Chinese Patent Application No. CN 201711331447.7, filed Dec. 13, 2017. The entire disclosures of the above applications are incorporated herein by reference.

FIELD OF INVENTION

The present invention relates to a crystal form and salt form of a TGF-βRI inhibitor, and a preparation method therefor, and further comprises the use of the crystal form and salt form in the preparation of a medicine for treating cancers.

PRIOR ARTS

Transforming growth factor-β (TGF-β) is a multi-functional growth factor superfamily with a wide range of biological activities, involving in early embryonic development, cartilage and bone formation, synthesis of extracellular matrix, inflammation, interstitial fibrosis, regulation of immune and endocrine functions, and tumor formation and development.

The TGF-β superfamily consists of a class of structurally and functionally related polypeptide growth factors, including TGF-βs (i.e., TGF-β in a narrow sense), activins, inhibins, and bone morphogenetic proteins (BMP) (i.e., mullerian), wherein the TGF-β is one of the important members of this family. In mammals, the TGF-β mainly exists in three forms: TGF-β1, TGF-β2 and TGF-β3, which are located on different chromosomes, among which the TGF-β1 accounts for the highest proportion (>90%) in somatic cells, and has the strongest activity, the most functions and the most widespread distribution. The newly synthesized TGF-β appears as an inactive precursor, which consists of three parts: a signal peptide, a latency-associated polypeptide (LAP) and a mature TGF-β. After enzymatic hydrolysis, an active TGF-β is formed and then binds to a receptor thereof to exert a biological effect.

TGF-β signaling molecules perform signal transduction through a transmembrane receptor complex. TGF-β receptors are transmembrane proteins that exist on the surface of cells. They are divided into type I receptors (TGF-βRI), type II receptors (TGF-βRII) and type III receptors (TGF-βRIII), wherein the TGF-βRI is also called activin receptor-like kinase 5 (ALK5). The TGF-βRIII lacks intrinsic activity, which is mainly related to the storage of the TGF-β. The TGF-βRI and the TGF-βRII belong to the serine/threonine kinase family. Type II receptors can bind to TGF-β ligands with higher affinity and form heterologous receptor complexes with type I receptors. A region rich in glycine and serine residues of the type I receptors (a GS domain) near the membrane is phosphorylated to initiate intracellular signaling cascade reactions.

Smads is an important TGF-β signal transduction and regulation molecule in the cell, which can directly transduce the TGF-β signal from the cell membrane into the cell nucleus. TGF-β/Smads signaling pathway plays an important role in the occurrence and development of tumors. In the TGF-β/Smads signal transduction, the activated TGF-β first binds to TGF-βRII on the cell membrane surface to form a heterodimeric complex, and TGF-βRI recognizes and binds to the binary complex.

The TGF-βRII phosphorylates the serine/threonine in the GS domain of the TGF-βRI cytoplasmic region, thereby activating the TGF-βRI; the activated TGF-βRI further phosphorylates the R-Smads (Smad2/Smad3) protein which then binds to Co-Smad (Smad4) to form a heterotrimeric complex, wherein the complex enters the nucleus and cooperates with other co-activators and co-inhibitors to regulate the transcription of target genes. Changes in any part of the TGF-β/Smads signaling pathway will result in abnormalities in the signal transduction pathway.

Current research shows that in tumor cells, the TGF-β may directly affect the tumor growth (extrinsic effects of the TGF-β signaling), or may indirectly affect the tumor growth (intrinsic effects of the TGF-β) by inducing epithelial-mesenchymal transition, blocking anti-tumor immune responses, increasing tumor-related fibrosis and enhancing vascular regeneration. Moreover, the TGF-β has a strong fibrosis induction effect and is an activator of fibroblasts associated with tumors. These fibroblasts are the main source of collagen type I and other fibrotic factors. The induced products of fibroblasts and other fibrotic factors may continue to create a microenvironment in which the immune response is reduced, drug resistance is increased and tumor angiogenesis is enhanced. In addition, the TGF-β affects angiogenesis during individual development and tumor growth. For example, TGF-βRI-deficient mouse embryos showed severe defects in vascular development, proving that the TGF-β signaling pathway is a key regulator in the development of vascular endothelium and smooth muscle cells.

In 2013, the FDA approved the small-molecule TGF-βRI inhibitor LY2157299 (WO 2002/094833) from Eli Lilly for the treatment of glioma and liver cancer. The LY2157299 is an orphan drug under development, named Galunisertib. The Galunisertib can not only inhibit the invasion and metastasis of tumor cells, but also inhibit the infiltration of tumor cells into blood vessels. In the phase 2 clinical trial for the treatment of liver cancer patients, after treatment with the Galunisertib, approximately 23% of patients had a decrease in serum alpha-fetoprotein (AFP) levels by at least 20%. Compared with patients who did not respond to AFP, these patients had slower tumor progression and longer survival span, and also increased expression of cadherin in epithelial cells, indicating that the Galunisertib may regulate ENT by inhibiting the TGF-β signaling pathway, thereby inhibiting liver cancer progression.

The structure of the Galunisertib (LY2157299) is as shown in formula (III):

(III)

In addition to the therapeutic efficacy, drug developers make attempts to provide suitable forms of active molecules with pharmaceutical properties, wherein the properties involve processing, manufacturing, storage stability, etc. Therefore, it has been found that forms with the desired properties are essential for drug development.

Content of the Present Invention

The present invention provides a crystal form A of a compound of formula (I), characterized in that the X-ray powder diffraction pattern thereof has characteristic diffraction peaks at the following 2θ angles: 9.553°±0.2°, 11.894°±0.2°, 17.502°±0.2°, 19.785°±0.2°, 24.072°±0.2° and 24.664°±0.2°.

(I)

In some embodiments of the present invention, the X-ray powder diffraction pattern of the above-mentioned crystal form A has characteristic diffraction peaks at the following 2θ angles: 9.553°±0.2°, 11.894°±0.2°, 15.370°±0.2°, 17.502°±0.2°, 19.785°±0.2°, 20.283°±0.2°, 24.072°±0.2° and 24.664°±0.2°.

Figure 1:
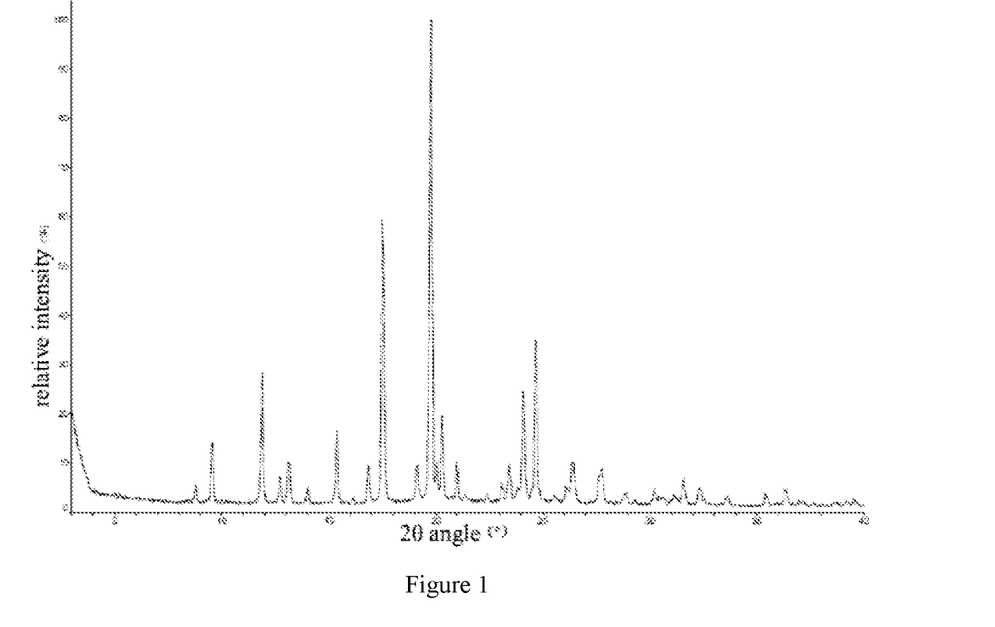
FIG. 1 is the XRPD pattern of the crystal form A of the compound of formula (I).

In some embodiments of the present invention, the X-ray powder diffraction pattern of the above-mentioned crystal form A is as shown in FIG. 1.

In some embodiments of the present invention, the XRPD pattern analysis data of the above-mentioned crystal form A is as shown in Table 1.

TABLE 1

| Serial number | 2θ angle (°) | Interplanar spacing (Å) | Relative intensity y (%) |
|---|---|---|---|
| 1 | 8.799 | 10.0419 | 3.6 |
| 2 | 9.553 | 9.2500 | 12.4 |
| 3 | 11.894 | 7.4343 | 27.4 |
| 4 | 12.727 | 6.9499 | 5.5 |
| 5 | 13.121 | 6.7421 | 8.5 |
| 6 | 14.024 | 6.3099 | 3.2 |
| 7 | 15.370 | 5.7600 | 15.2 |
| 8 | 16.155 | 5.4819 | 1.3 |
| 9 | 16.850 | 5.2573 | 7.6 |
| 10 | 17.502 | 5.0628 | 59.1 |
| 11 | 19.132 | 4.6351 | 6.7 |
| 12 | 19.785 | 4.4837 | 100 |
| 13 | 20.027 | 4.4299 | 7.3 |
| 14 | 20.283 | 4.3746 | 17.1 |
| 15 | 20.742 | 4.2789 | 0.8 |
| 16 | 20.992 | 4.2285 | 7.7 |
| 17 | 21.366 | 4.1553 | 1.4 |
| 18 | 22.376 | 3.9700 | 1.4 |
| 19 | 23.099 | 3.8472 | 3 |
| 20 | 23.437 | 3.7925 | 7 |
| 21 | 23.850 | 3.7278 | 2.1 |
| 22 | 24.072 | 3.6939 | 22.7 |
| 23 | 24.664 | 3.6066 | 33.2 |
| 24 | 25.552 | 3.4832 | 1.1 |
| 25 | 26.119 | 3.4089 | 3.2 |
| 26 | 26.361 | 3.3781 | 8.4 |
| 27 | 27.756 | 3.2114 | 7.4 |
| 28 | 28.447 | 3.1350 | 0.5 |

TABLE 1-continued

| Serial number | 2θ angle (°) | Interplanar spacing (Å) | Relative intensity y (%) |
|---|---|---|---|
| 29 | 28.864 | 3.0907 | 2.2 |
| 30 | 29.285 | 3.0471 | 0.8 |
| 31 | 30.186 | 2.9582 | 2.9 |
| 32 | 30.442 | 2.9339 | 1.5 |
| 33 | 31.119 | 2.8716 | 1.8 |
| 34 | 31.565 | 2.8320 | 5.2 |
| 35 | 32.298 | 2.7694 | 3.4 |
| 36 | 33.616 | 2.6638 | 2 |
| 37 | 35.382 | 2.5348 | 2.5 |
| 38 | 36.32 | 2.4714 | 3.4 |
| 39 | 36.952 | 2.4306 | 0.9 |
| 40 | 39.143 | 2.2994 | 1 |
| 41 | 39.484 | 2.2804 | 1.3 |

In some embodiments of the present invention, the above-mentioned crystal form A may also be characterized by DSC, with an initial temperature of 266.07° C. and a peak temperature of 271.79° C.

In some embodiments of the present invention, the differential scanning calorimetry profile of the above-mentioned crystal form A has an endothermic peak at 271.79° C.±3° C.

Figure 2:
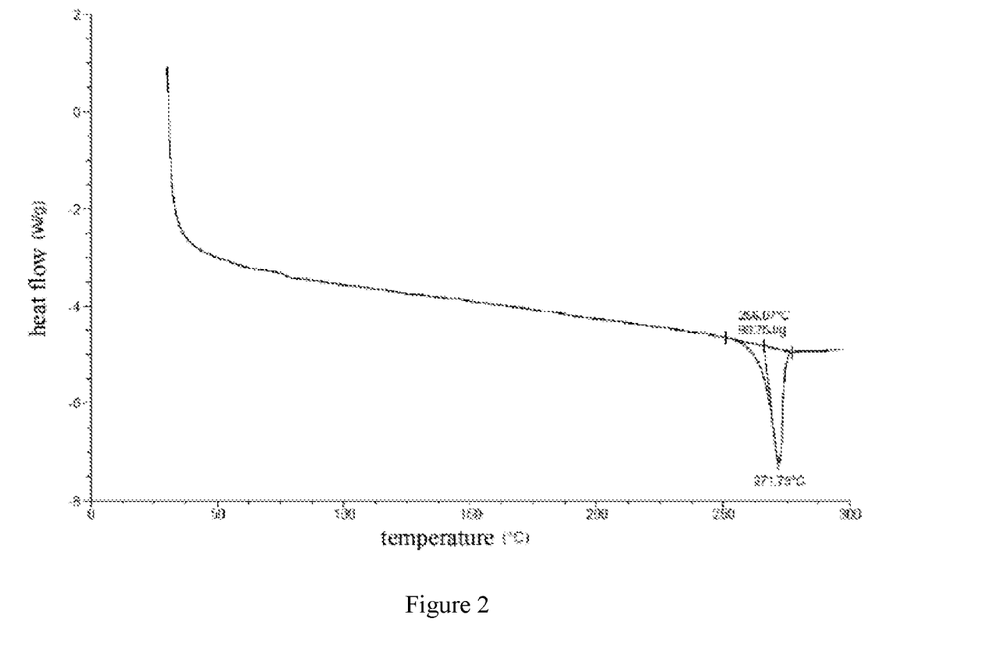
FIG. 2 is the DSC pattern of the crystal form A of the compound of formula (I).

In some embodiments of the present invention, the differential scanning calorimetry profile pattern of the above-mentioned crystal form A is as shown in FIG. 2.

In some embodiments of the present invention, the above-mentioned crystal form A may also be characterized by TGA, wherein the TGA pattern shows that when the crystal form is heated to 110.82° C., the weight is reduced by 0.1075%; when heated to 229.08° C., the weight is further reduced by 0.9974%; there occurs a larger weight loss after 229.08° C.

In some embodiments of the present invention, the thermogravimetric analysis profile of the above-mentioned crystal form A shows 0.1075% of weight loss at 110.82° C.±3° C. and 1.105% of weight loss at 229.08° C.±3° C.

Figure 3:
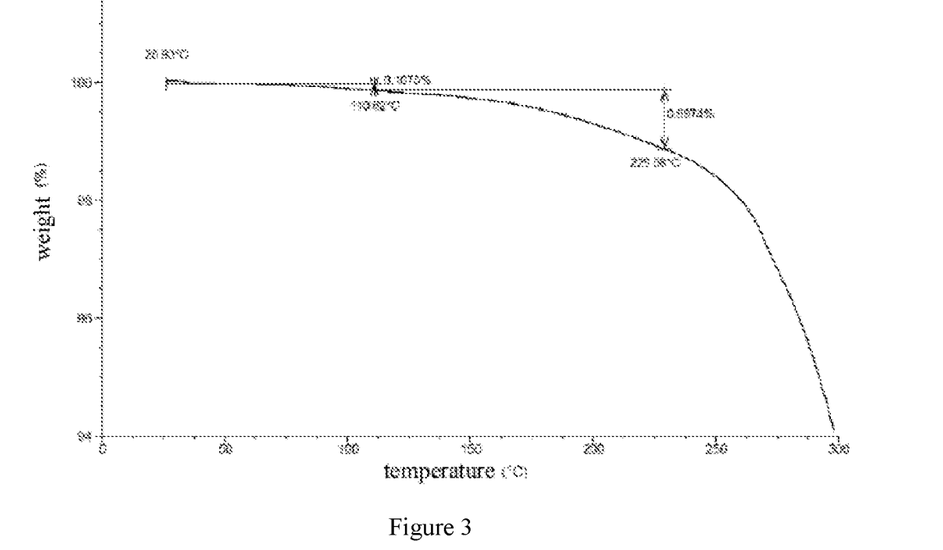
FIG. 3 is the TGA pattern of the crystal form A of the compound of formula (I).

In some embodiments of the present invention, the thermogravimetric analysis profile pattern of the above-mentioned crystal form A is as shown in FIG. 3.

The present invention further provides a compound of formula (II).

(II)

The present invention further provides a crystal form B of the compound of formula (II), characterized in that the X-ray powder diffraction pattern thereof has characteristic diffraction peaks at the following 2θ angles: 13.349°±0.2°, 19.012°±0.2°, 20.235°±0.2° and 23.370°±0.2°.

In some embodiments of the present invention, the X-ray powder diffraction pattern of the above-mentioned crystal form B has characteristic diffraction peaks at the following 2θ angles: 13.349±0.2°, 15.066±0.2°, 16.782±0.2°, 19.012±0.2°, 20.235±0.2°, 22.027±0.2°, 23.370±0.2° and 27.253±0.2°.

Figure 4:
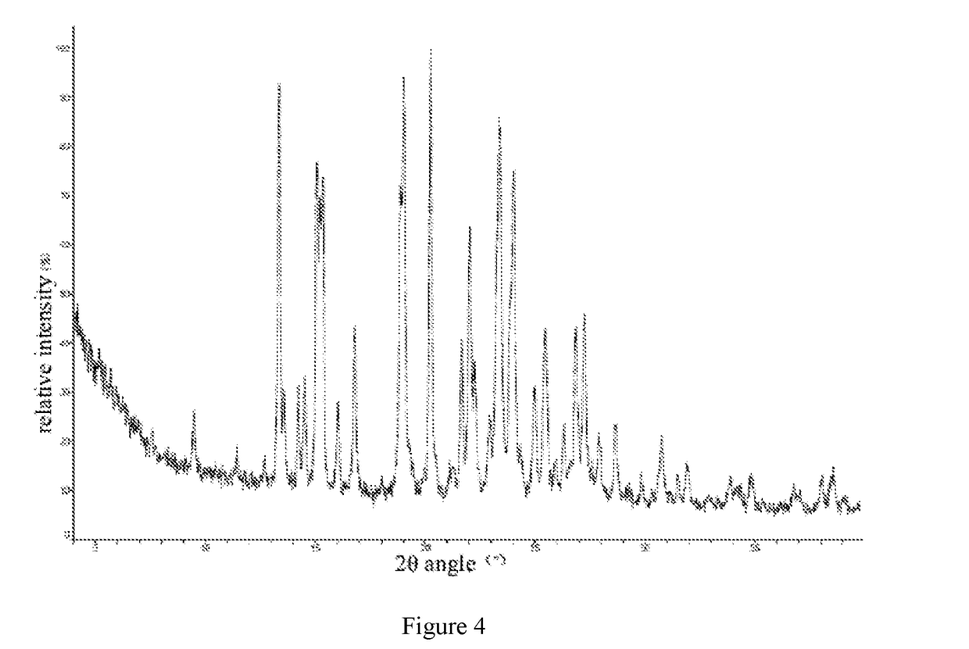
FIG. 4 is the XRPD pattern of the crystal form B of the compound of formula (II).

In some embodiments of the present invention, the X-ray powder diffraction pattern of the above-mentioned crystal form B is as shown in FIG. 4.

In some embodiments of the present invention, the XRPD pattern analysis data of the above-mentioned crystal form B is as shown in Table 2.

TABLE 2

| Serial number | 2θ angle (°) | Interplanar spacing (Å) | Relative intensity y (%) |
|---|---|---|---|
| 1 | 9.469 | 9.3321 | 13.6 |
| 2 | 13.349 | 6.6271 | 89.7 |
| 3 | 13.568 | 6.5209 | 20.7 |
| 4 | 14.219 | 6.2235 | 21.1 |
| 5 | 14.512 | 6.0986 | 23.2 |
| 6 | 15.066 | 5.8758 | 71.9 |
| 7 | 15.339 | 5.7719 | 68.9 |
| 8 | 16.029 | 5.5247 | 19.2 |
| 9 | 16.782 | 5.2784 | 37.3 |
| 10 | 19.012 | 4.6642 | 93.6 |
| 11 | 20.235 | 4.3849 | 100 |
| 12 | 21.669 | 4.0978 | 34 |
| 13 | 22.027 | 4.032 | 58.8 |
| 14 | 22.229 | 3.9959 | 28.6 |
| 15 | 23.370 | 3.8033 | 81.3 |
| 16 | 24.984 | 3.5612 | 22.2 |
| 17 | 25.442 | 3.498 | 34.9 |
| 18 | 26.843 | 3.3186 | 34.5 |
| 19 | 27.253 | 3.2696 | 37.9 |
| 20 | 27.905 | 3.1946 | 12 |
| 21 | 28.639 | 3.1144 | 16.5 |
| 22 | 30.745 | 2.9057 | 14.8 |
| 23 | 31.895 | 2.8035 | 9.1 |
| 24 | 33.883 | 2.6434 | 6.7 |
| 25 | 34.373 | 2.6068 | 5 |
| 26 | 34.831 | 2.5736 | 7.6 |
| 27 | 36.765 | 2.4426 | 5.8 |
| 28 | 37.057 | 2.424 | 4.2 |
| 29 | 38.061 | 2.3623 | 7.7 |
| 30 | 38.576 | 2.332 | 9.3 |

In some embodiments of the present invention, the above-mentioned crystal form B may also be characterized by DSC, which has an endothermic peak at 234.43° C.±3° C.

In some embodiments of the present invention, the differential scanning calorimetry profile of the above-mentioned crystal form B has an endothermic peak at 234.43° C.±3° C.

Figure 5:
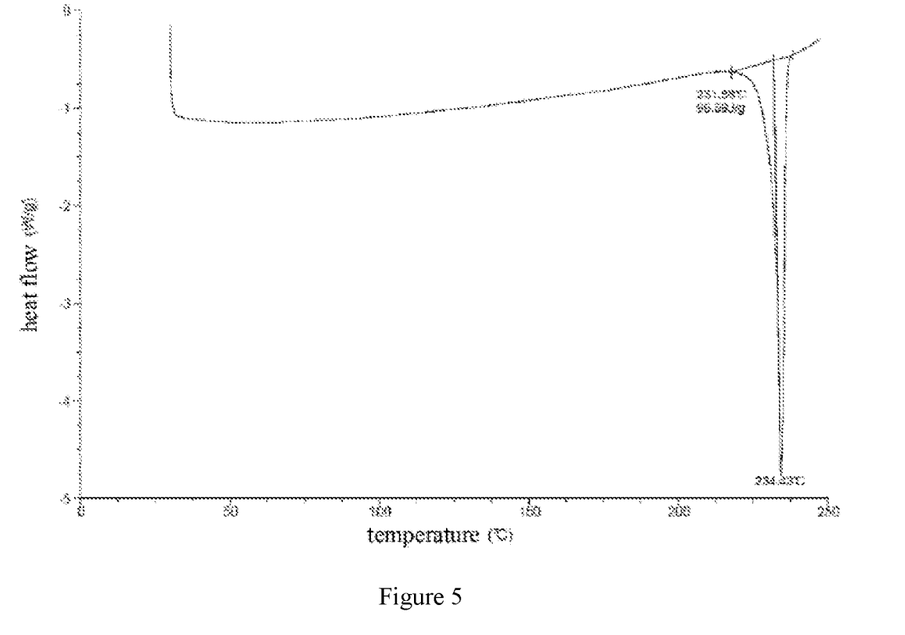
FIG. 5 is the DSC pattern of the crystal form B of the compound of formula (II).

In some embodiments of the present invention, the differential scanning calorimetry profile pattern of the above-mentioned crystal form B is as shown in FIG. 5.

In some embodiments of the present invention, the above-mentioned crystal form B may also be characterized by TGA, wherein the TGA pattern shows that when the crystal form is heated to 120° C., the weight is reduced by 0.3043%; when heated to 238.46° C., the weight is further reduced by 1.295%.

In some embodiments of the present invention, the thermogravimetric analysis profile of the above-mentioned crystal form B shows 0.3043% of weight loss at 120° C.±3° C. and 1.599% of weight loss at 238.46° C.±3° C.

Figure 6:
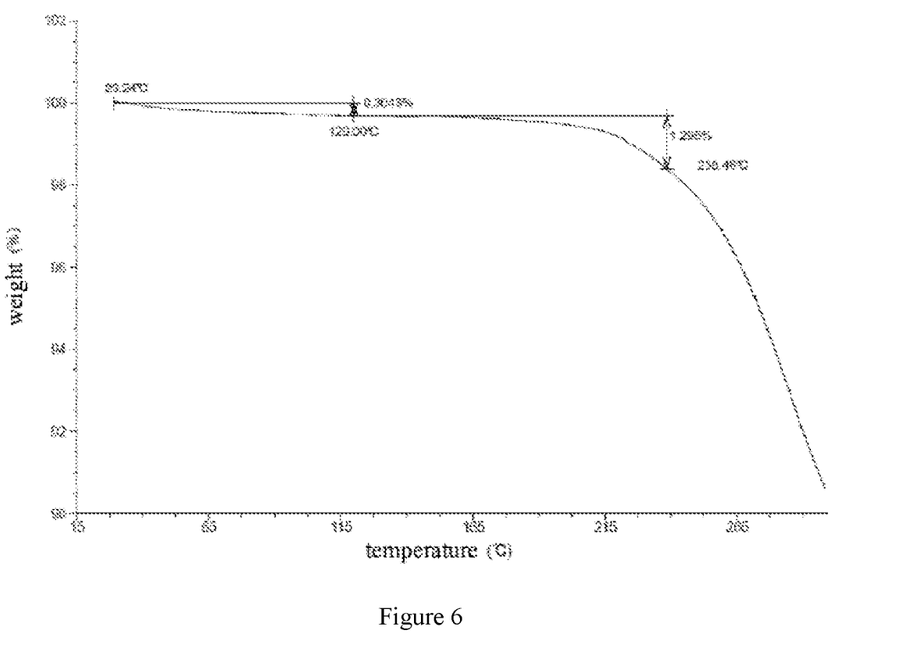
FIG. 6 is the TGA pattern of the crystal form B of the compound of formula (II).

In some embodiments of the present invention, the thermogravimetric analysis profile pattern of the above-mentioned crystal form B is as shown in FIG. 6.

The present invention further provides a hydrochloride, sulfate and methanesulfonate of the compound of formula (I).

In some embodiments of the present invention, the above-mentioned hydrochloride is

(IV)

In some embodiments of the present invention, the above-mentioned sulfate is (V)

In some embodiments of the present invention, the above-mentioned methanesulfonate is (VI)

The present invention further provides the use of the above-mentioned compounds or crystal forms in the preparation of a medicine for treating cancers.

TECHNICAL EFFECTS

The process for preparing the salt form and crystal form provided in the present invention is simple; moreover, the crystal form is stable under the conditions of high temperature and high humidity and is slightly hygroscopic, and the salt form has good solubility in pure water and a biological vehicle and has good prospects for preparation.

DEFINITION AND DESCRIPTION

Unless otherwise stated, the following terms and phrases used herein are intended to have the following meanings. A specific phrase or term should not be considered uncertain or unclear unless specifically defined, but should be understood in an ordinary meaning. When a trade name appears herein, it is intended to refer to the corresponding commodity or an active ingredient thereof.

The intermediate compounds of the present invention can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present invention.

The chemical reactions described in the specific embodiments of the present invention are completed in a suitable solvent, wherein the solvent must be suitable for the chemical changes of the present invention and the reagents and materials required thereby. In order to obtain the compounds of the present invention, sometimes a person skilled in the art needs to modify or select synthesis steps or reaction schemes based on the existing embodiments.

The present invention will be specifically described below by way of examples which are not intended to limit the present invention in any way.

All solvents used in the present invention are commercially available and can be used without further purification.

The following abbreviations are used in the present invention: r.t. represents room temperature; aq represents aqueous solution; eq represents equivalent; DCM represents dichloromethane; THF represents tetrahydrofuran; DMSO represents dimethyl sulfoxide; DMF represents N,N-dimethylformamide; EtOAc represents ethyl acetate; EtOH represents ethanol; MeOH represents methanol; dioxane represents dioxane; HOAc represents acetic acid; DIPEA represents diisopropylethylamine; TEA or Et$_3$N represents triethylamine; Na$_2$CO$_3$ represents sodium carbonate; K$_2$CO$_3$ represents potassium carbonate; NaHCO$_3$ represents sodium bicarbonate; Na$_2$SO$_4$ represents sodium sulfate; NaOH represents sodium hydroxide; LiHMDS represents lithium bis(trimethylsilyl)amine; Pd(dppf)Cl$_2$ represents [1,1'-bis(diphenylphosphino)ferrocene]palladium dichloride; Xphos represents 2-dicyclohexylphosphino-2',4',6'-triisopropylbiphenyl; Xphos-PD-G$_2$ represents chloro(2-dicyclohexylphosphino-2',4',6'-triisopropyl-1,1'-biphenyl) [2-(2'-amino-1,1'-biphenyl)palladium (II); NBS represents N-bromosuccinimide; HCl represents hydrochloric acid; H$_2$SO$_4$ represents sulfuric acid; ° C. represents degree centigrade.

Compounds are named by hand or ChemDraw® software, and commercially available compounds named by the supplier catalog names.

Instrument and Analysis Method

In the present invention, the X-ray powder diffractometer (XRPD) is determined by using the following method:
instrument model: Bruker D8 advance X-ray diffractometer;
test method: approximately 10-20 mg of sample is used for XRPD detection.
The detailed XRPD parameters are as follows:
X-ray tube: Cu, kα, (λ=1.54056Å);
tube voltage: 40 kV, tube current: 40 mA;
divergence slit: 0.60 mm;
detector slit: 10.50 mm;
anti-scatter slit: 7.10 mm;
scanning range: 3-40 deg or 4-40 deg;
step size: 0.02 deg;
step length: 0.12 sec;
sample disk rotating speed: 15 rpm.

In the present invention, the differential scanning calorimeter (DSC) is determined by using the following method:
instrument model: TA Q2000 differential scanning calorimeter.
Test method: place about 1 mg of sample in a DSC aluminum pan for testing; under the condition of 50 mL/min of nitrogen, heat the sample from 30° C. (room temperature) to 300° C. (or 350° C.) at a heating rate of 10° C./min.

In the present invention, the thermal gravimetric analyzer (TGA) is determined by using the following method:
instrument model: TA Q5000 thermogravimetric analyzer.
Test method: place 2-5 mg of sample in a TGA platinum pan for testing; under the condition of 25 mL/min N$_2$, heat the sample from room temperature to 300° C. or to 20% of weight loss at a heating rate of 10° C./min.

In the present invention, the dynamic vapor sorption (DVS) is determined by using the following method:
instrument model: SMS DVS Advantage dynamic vapor sorption instrument
Test condition: place 10-15 mg of sample in a DVS sample disk for testing.
The detailed DVS parameters are as follows:
temperature: 25° C.
balance: dm/dt=0.01%/min (minimum: 10 min; maximum: 180 min)
drying: dry for 120 min at 0% RH
RH (%) test step: 10%
RH (%) test step range: 0%-90%-0%
The classification of hygroscopicity evaluation is as follows:

| Classification of hygroscopicity | Hygroscopic weight gain* |
|---|---|
| Deliquescence | Absorbing enough moisture to form a liquid |
| Extremely hygroscopic | ΔW % ≥ 15% |
| Hygroscopic | 15% ≥ ΔW % ≥ 2% |
| Slightly hygroscopic | 2% ≥ ΔW % ≥ 0.2% |
| Not or almost not hygroscopic | ΔW % < 0.2% |

*Hygroscopic weight gain (ΔW %) at 25° C. ± 1° C. and 80% ± 2% RH

DETAILED DESCRIPTION OF EMBODIMENTS

In order to better understand the content of the present invention, the following specific examples are used for further description, but the specific embodiments do not limit the content of the present invention.

Example 1 Preparation of a Compound of Formula (I)

(I)

Preparation of Intermediates 1-6

1-6

Step A: Ethyl acetate (291.41 ml, 2.98 mol) was dissolved in toluene (750.00 ml), and then sodium ethoxide (135.06 g, 1.98 mol) was added portionwise at room temperature thereto, and the reaction mixture was stirred at room temperature for 1 hour. 1-1 (150.00 g, 992.33 mmol) was added to the above-mentioned reaction solution at 25° C., and then heated to 95° C. and stirred for 15 hours. The reaction mixture was cooled to about 30° C., adjusted to pH 7 with acetic acid, diluted with water (500 ml), and then extracted with ethyl acetate (500 ml). The organic phase was dried over anhydrous sodium sulfate, filtered and concentrated under reduced pressure. The residue was purified by a silica gel column (eluent: petroleum ether/ethyl acetate v/v=50/1) to afford 1-2.

Step B: 1-2 (120.00 g, 579.07 mmol) was dissolved in pyridine (300 ml), and then p-toluenesulfonate salt (172.01 g, 631.66 mmol) of 1-aminopyrrolidine-2-one was added thereto. The reaction mixture was stirred at 25° C. for 16 hours, and then concentrated under reduced pressure to remove the solvent. The residue was diluted with water (300 ml), and then extracted with ethyl acetate (300 ml×2). The combined organic phase was dried over anhydrous sodium sulfate, filtered and concentrated under reduced pressure to afford 1-3.

Step C: 1-3 (155.00 g, 535.72 mmol) was dissolved in toluene, and then sodium ethoxide (72.91 g, 1.07 mol) was added thereto. The reaction mixture was heated to 100° C. and stirred for 16 hours, and subsequently cooled to room temperature. The reaction mixture was slowly diluted with water (1.5 L), adjusted to pH 4 with concentrated hydrochloric acid, and extracted with dichloromethane/isopropanol (v/v=10/1, 1 L×7). The combined organic phase was dried over anhydrous sodium sulfate, filtered and concentrated under reduced pressure. The residue was slurried with petroleum ether/ethyl acetate (v/v=10/1, 200 ml) and filtered, and the solid was collected. The solid was dried under reduced pressure to afford 1-4.

Step D: 1-4 (45.00 g, 184.99 mmol) was dissolved in N,N-dimethylformamide (650.00 ml), and then NBS (49.09 g, 258.99 mmol) was added thereto. The reaction mixture was stirred at 30° C.-40° C. for 60 hours, and then diluted with water (600 ml) and extracted with dichloromethane/isopropanol (v/v=10/1, 500 ml×3). The combined organic phase was washed once with sodium hydroxide (0.5 mol/L, 800 ml), dried over anhydrous sodium sulfate, filtered and concentrated under reduced pressure. The resulting solid was slurried with petroleum ether/ethyl acetate (v/v=10/1, 200 ml) and filtered, and the solid was collected. The solid was dried under reduced pressure to afford 1-5.

Step E: 1-5 (1.00 g, 3.60 mmol) and triisopropyl borate (1.79 g, 9.54 mmol) were dissolved in tetrahydrofuran (20.00 ml). The reaction mixture was cooled to minus 70° C., and then n-butyl lithium (2.5 M, 3.74 ml) was added dropwise. After the dropwise addition was complete, the reaction mixture was stirred at 25° C. for 1 hour, and then adjusted to pH 7 with aqueous hydrochloric acid (0.5 mol/L). Then the reaction mixture was concentrated under reduced pressure to remove tetrahydrofuran, and then cooled to 15° C. The mixture was filtered, and the filter cake was slurried with petroleum ether/ethyl acetate (v/v=10/1, 5.5 ml) and filtered, and the solid was collected which was dried under reduced pressure to afford 1-6.

Preparation of a Compound of Formula (I)

Step A: 1-7 (16.00 g, 65.30 mmol) was dissolved in tetrahydrofuran (800.00 ml), and after cooling to minus 60° C.-minus 70° C., lithium hexamethyldisilazide (1 mol/L, 130.60 ml, 65.30 mmol) was added dropwise thereto. The reaction mixture was stirred at minus 60° C.-minus 70° C. for 15 minutes, and N,N-dimethylformamide (14.32 g, 195.90 mmol, 15.07 ml) was added thereto. Then the reaction mixture was stirred continuously at minus 60° C.-minus 70° C. for 15 minutes, and subsequently quenched with saturated aqueous ammonium chloride solution (500 ml). The reaction mixture was warmed to room temperature, and then extracted with ethyl acetate (500 ml×2). The combined organic phase was washed with brine (500 ml), dried over anhydrous sodium sulfate, filtered and concentrated under reduced pressure. The residue was purified by a silica gel column (eluent: dichloromethane/ethyl acetate v/v=10/1) to afford 1-8. $^1$H NMR (400 MHz, DMSO-d6) δ 10.46 (s, 1H), 8.62 (s, 1H), 8.16 (d, J=9.3 Hz, 1H), 7.88 (d, J=9.3 Hz, 1H).

Step B: In a 500-ml three-necked flask equipped with a thermometer and a nitrogen balloon, 2-diethoxyphosphoryl acetonitrile (3.83 g, 21.61 mmol, 3.48 ml) and tetrahydrofuran (80 ml) were added. The mixture was cooled to 0° C., and then potassium tert-butoxide (2.42 g, 21.61 mmol) was added portionwise thereto. The reaction mixture was stirred at 0° C. for 15 minutes, and then added dropwise to another suspension (1-8 was dispersed in tetrahydrofuran (120 ml) and cooled to 0° C.) through a dropping funnel. The reaction mixture was stirred at 0° C. for 15 minutes, and then poured into water (300 ml) and quenched, and extracted with ethyl acetate (200 ml) and dichloromethane (200 ml×2). The combined organic phase was washed with brine (300 ml), dried over anhydrous sodium sulfate, filtered and concentrated under reduced pressure. The residue was purified by a silica gel column (eluent: dichloromethane/ethyl acetate v/v=200/1 to 10/1) to afford 1-9. $^1$H NMR (400 MHz, CDCl$_3$) δ 8.42 (s, 1H), 8.03 (d, J=9.3 Hz, 1H), 7.98-7.91 (m, 1H), 7.85-7.78 (m, 1H), 7.60 (d, J=9.2 Hz, 1H).

Step C: 1-9 (4.50 g, 15.20 mmol), 1-6 (4.43 g, 18.24 mmol), sodium carbonate (4.83 g, 45.60 mmol), [1,1'-bis(diphenylphosphino)ferrocene]palladium dichloride (556.07 mg, 759.96 μmol), 2-dicyclohexylphosphino-2',6'-dimethoxybiphenyl (311.98 mg, 759.96 μmol), and [2-(2-aminophenyl)phenyl]-chloro-palladium-cyclohexyl-[2-(2,6-dimethoxyphenyl)phenyl]phosphine (547.64 mg, 759.96 μmol) were added to the mixed solvent of dioxane (100 ml) and water (20 ml). The mixture was ventilated with nitrogen three times and then heated to 90° C.-100° C. and stirred for 2 hours. The reaction mixture was poured into water (200 ml) and quenched, and extracted with dichloromethane (200 ml×2). The combined organic phase was washed with brine (200 ml), dried over anhydrous sodium sulfate, filtered and concentrated under reduced pressure. The residue was purified by a silica gel column (eluent: dichloromethane/methanol, v/v=30/1) to afford a crude product, which was stirred for 12 hours in the mixed solvent of petroleum ether/ethyl acetate (v/v=5/1) and filtered, and the solid was collected which was concentrated and dried under reduced pressure to afford 1-10. $^1$H NMR (400 MHz, CDCl$_3$) δ 8.49 (s, 1H), 7.82-7.74 (m, 2H), 7.59-7.46 (m, 4H), 6.99 (dd, J=2.6, 6.1 Hz, 1H), 4.39 (d, J=6.3 Hz, 2H), 2.90-2.70 (m, 4H), 2.20 (s, 3H).

Step D: 1-10 (5.37 g, 14.62 mmol) was dissolved in the mixed solvent of dichloromethane (20 ml), dimethyl sulfoxide (70 ml) and water (20 ml), and then hydrogen peroxide (8.29 g, 73.10 mmol, 7.02 ml, 30%) and sodium hydroxide (2 mol/L, 14.62 ml) were respectively added thereto. The mixture was stirred at 15° C.-20° C. for 12 hours. The mixture was poured into water (200 ml) and quenched, and extracted with the mixed solvent of dichloromethane/isopropanol (3/1) (200 ml×1). The organic phase was washed with saturated aqueous sodium thiosulfate solution (200 ml), dried over anhydrous sodium sulfate, filtered and concentrated under reduced pressure. The residue was purified by preparative high performance liquid chromatography (column: Phenomenex Gemini C18 250×50 mm×10 μm; mobile phase: [water (0.05% ammonia v/v)-acetonitrile]; gradient: 5%-32%, 33; 80% minutes) to afford the compound of formula (I). $^1$H NMR (400 MHz, CDCl$_3$) δ 8.45 (s, 1H), 8.09 (d, J=15.6 Hz, 1H), 7.85 (d, J=15.6 Hz, 1H), 7.69 (d, J=9.2 Hz, 1H), 7.55-7.45 (m, 2H), 7.37 (d, J=7.8 Hz, 1H), 6.99 (d, J=7.7 Hz, 1H), 5.93-5.65 (m, 2H), 4.35 (br. s., 2H), 2.99-2.64 (m, 4H), 2.33 (s, 3H).

Example 2 Preparation of a Compound of Formula (II)

(II)

115 mg of the compound of formula (I) was added to a 8-ml glass bottle and 4 ml of tetrahydrofuran was added thereto, which form a suspension by ultrasonic-assisted solubilization; and then 1.05 equivalents of p-toluenesulfonic acid monohydrate was slowly added. The above-mentioned suspended sample was placed on a magnetic stirrer (40° C.) and stirred for 16 hours. The sample solution was centrifuged, and the solid was taken and placed in a vacuum oven at 35° C. for drying for 16 hours to afford the compound of formula (II). $^1$H NMR (400 MHz, CD$_3$OD) δ 8.61 (s, 1H), 8.14 (t, J=8.0 Hz, 1H), 8.05 (d, J=15.6 Hz, 1H), 7.90 (d, J=8.8 Hz, 1H), 7.70 (dd, J=8.4, 15.6 Hz, 4H), 7.54 (d, J=15.6 Hz, 1H), 7.39 (d, J=8.0 Hz, 1H), 7.20 (d, J=7.6 Hz, 2H), 4.42 (m, 2H), 3.05-2.87 (m, 2H), 2.82 (s, 3H), 2.81-2.74 (m, 2H), 2.35 (s, 3H).

Example 3 Preparation of a Compound of Formula (IV)

(IV)

115 mg of the compound of formula (I) was added to a 8-ml glass bottle and 4 ml of tetrahydrofuran was added thereto, which form a suspension by ultrasonic-assisted solubilization; and then 1.05 equivalents of hydrochloric acid was slowly added. The above-mentioned suspended sample was placed on a magnetic stirrer (40° C.) and stirred for 16 hours. The sample solution was centrifuged, and the solid was taken and placed in a vacuum oven at 35° C. for drying for 16 hours. The resulting solid was added to an appropriate amount of acetone to prepare a suspension, stirred at 40° C. and then centrifuged to discard the supernatant, and the solid sample was dried with an oil pump at room temperature to afford the compound of formula (IV).

Example 4 Preparation of a Compound of Formula (V)

(V)

115 mg of the compound of formula (I) was added to a 8-ml glass bottle and 4 ml of tetrahydrofuran was added thereto, which form a suspension by ultrasonic-assisted solubilization; and then 1.05 equivalents of sulfuric acid was slowly added. The above-mentioned suspended sample was placed on a magnetic stirrer (40° C.) and stirred for 16 hours. The sample solution was centrifuged, and the solid was taken and placed in a vacuum oven at 35° C. for drying for 16 hours to afford the compound of formula (V).

Example 5 Preparation of a Compound of Formula (VI)

(VI)

115 mg of the compound of formula (I) was added to a 8-ml glass bottle and 4 ml of tetrahydrofuran was added thereto, which form a suspension by ultrasonic-assisted solubilization; and then 1.05 equivalents of methanesulfonic acid was slowly added. The above-mentioned suspended sample was placed on a magnetic stirrer (40° C.) and stirred for 16 hours. The sample solution was centrifuged, and the solid was taken and placed in a vacuum oven at 35° C. for drying for 16 hours to afford the compound of formula (VI).

Example 6 Preparation of Crystal Form A of the Compound of Formula (I)

10 g of the compound of formula (I) was taken and placed in the mixed solvent of ethanol (80 ml) and water (40 ml), heated to 70° C.-75° C. and stirred until clear, and then filtered while hot; the filtrate was distilled under reduced pressure until the volume of the remaining solution was about 50 ml, and then cooled and allowed to stand for crystallization, and filtered; the resulting filter cake was dried under reduced pressure, and the solid obtained therefrom was the crystal form A of the compound of formula (I).

Example 7 Preparation of Crystal Form B of the Compound of Formula (II)

192 mg of the compound of formula (I) was weighed and added to a glass bottle. 10 ml of the mixed solvent of tetrahydrofuran:acetic acid (v/v=9/1) was added, and after 30 minutes of ultrasonic-assisted solubilization, the sample was dissolved into a clear solution. The solution was placed on a magnetic stirrer (40° C.) and stirred. After slowly adding 1.05 equivalents of p-toluenesulfonic acid monohydrate, the sample was stirred overnight. After naturally cooling to room temperature, the supernatant was discarded by centrifugation; 10 ml of tetrahydrofuran was added and stirred for half an hour, and then the supernatant was discarded again by centrifugation; the same process was repeated twice. The resulting solid was placed in a vacuum oven at 40° C. for drying for 1 hour, and was further dried in the vacuum oven at 30° C. for 16 hours after crush, affording the crystal form B of the compound of formula (II).

Example 8 TGFβ-RI Receptor Binding Activity Screening Protocol In Vitro

1. Experimental Method:
1) Compound to be tested: $IC_{50}$ was determined by a method of 10 gradient points with three-fold dilution each, and the initial concentration was 5 μM.

2) The reaction system contained 10 μM of ATP.
3) When the percentage of enzyme activity of the sample at the highest concentration (compared to the solvent group) was less than 65%, the curve fitting was performed to calculate the $IC_{50}$ value.

2. The Experimental Results are Shown in the Table Below:

| Sample | TGF-βRI $IC_{50}$ (nM) |
|---|---|
| LY2157299 | 208 |
| Compound of formula (I) | 40 |

Conclusion: The TGF-βRI inhibition activity of the compound of formula (I) is better than that of LY2157299 under the same experimental conditions as described above.

Example 9 Study on the Solubility of Different Salt Types of the Compound of Formula (I) in Biological Vehicle 1 ml of biological vehicle solution (FaSSIF, FeSSIF and SGF) was pipetted respectively into a 1.5-ml glass bottle, and then added to the above-mentioned solution at a gradient of 2 mg until 10 mg or the mixture was saturated. The mixture was prepared in 2 parts in parallel, and then shaken at 37° C. Samples were taken after 4 hours and 24 hours, respectively. The samples taken were centrifuged quickly, and the supernatant was measured for pH value and diluted with a diluent to a suitable multiple, and then the concentration was determined by HPLC. The test results are as shown in Table 3 below.

TABLE 3

Solubility of different salt types of the compound of formula (I) in biological vehicle

| Condition | | State and pH value | | | | Concentration (mg/mL) | |
|---|---|---|---|---|---|---|---|
| | | 4 hours | 4 hours | 24 hours | 24 hours | 4 hours | 24 hours |
| Compound of | SGF | soluble | 2.37 | soluble | 2.43 | 1.997 | 1.994 |
| formula (I) | FeSSIF | turbid | 4.97 | turbid | 4.95 | 0.565 | 0.637 |
| (free base) | FaSSIF | turbid | 6.45 | turbid | 6.42 | 0.352 | 0.421 |
| Hydrochloride | SGF | soluble | 2.04 | soluble | 2.05 | 4.343 | 4.427 |
| | FeSSIF | turbid | 4.52 | turbid | 4.52 | 1.028 | 1.065 |
| | FaSSIF | soluble | 3.96 | soluble | 3.97 | 4.378 | 4.195 |
| Sulphate | SGF | soluble | 1.77 | soluble | 1.84 | 4.885 | 4.952 |
| | FeSSIF | turbid | 4.22 | turbid | 4.21 | 1.530 | 1.504 |
| | FaSSIF | soluble | 2.44 | soluble | 2.50 | 4.998 | 5.000 |
| Methanesulfonate | SGF | soluble | 2.08 | soluble | 2.14 | 5.103 | 5.163 |
| | FeSSIF | turbid | 4.58 | turbid | 4.60 | 0.852 | 0.925 |
| | FaSSIF | soluble | 4.16 | turbid | 3.71 | 5.159 | 3.704 |
| Compound of | SGF | Suspension | 3.45 | Suspension | 4.26 | 1.61 | 1.47 |
| formula (II) | FeSSIF | clear | 1.89 | clear | 1.87 | 10.84 | 10.58 |
| (p)-toluenesulfonate) | FaSSIF | clear | 3.15 | clear | 3.13 | 10.15 | 10.72 |

[Note]:
SGF represents simulated gastric fluid; FaSSIF represents fasted-state simulated intestinal fluid; FeSSIF represents fed-state simulated intestinal fluid.
Conclusion: It can be seen from the results in the table above that the solubility of the compound of formula (II) in biological vehicle is significantly improved compared to the compound of formula (I).

Example 10 Study on the Solubility of the Compounds of Formula (I) and Formula (II) in Water 2 mg of the sample of each compound was weighed and added to a 1.5-ml glass vial, and a certain volume of pure water was added with a pipette, and ultrasonic solubilization was performed appropriately. The study was conducted at room temperature and tested for solubilization. The approximate solubility results are as follows:

| Sample | Amount of pure water added (μL) | Approximate solubility S (mg/mL) |
| --- | --- | --- |
| Compound of formula (I) | >1000 | S < 1.9 |
| Compound of formula (II) | 20-40 | 49.0 < S < 98.0 |

Conclusion: The approximate solubility of the compound of formula (II) in pure water is significantly improved compared to the compound of formula (I).

Example 11 Study on Hygroscopicity of the Crystal Form B of the Compound of Formula (II)

Figure 7:
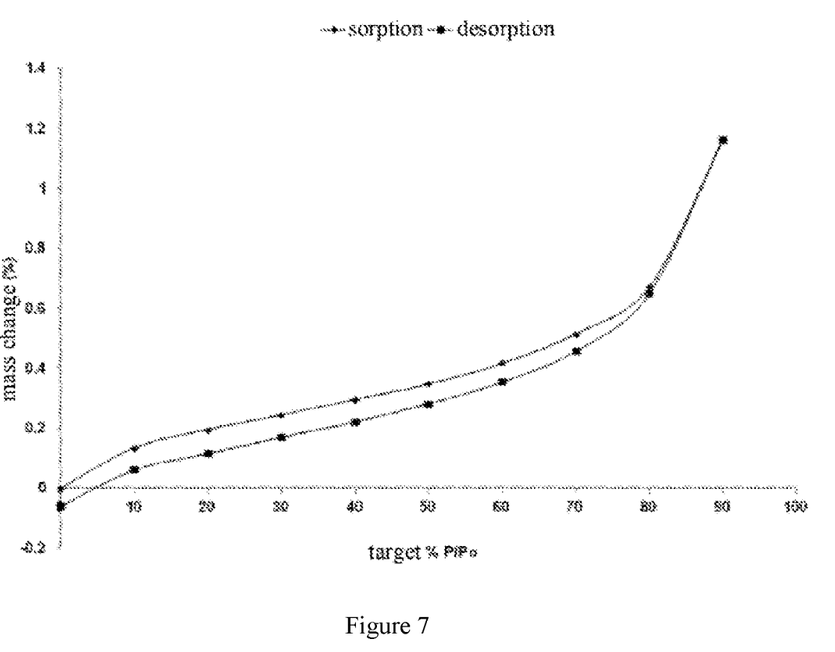
FIG. 7 is the DVS pattern of the crystal form B of the compound of formula (II).

1. Experimental material: SMS DVS Advantage dynamic vapor sorption instrument
2. Experimental method: an appropriate amount of the crystal form B of the compound of formula (II) was placed in a DVS sample disk for DVS analysis.
3. Experimental result: the DVS pattern of the crystal form B of the compound of formula (II) was shown in FIG. 7, with ΔW=0.673%.

Conclusion: The hygroscopic weight gain of the crystal form B of the compound of formula (II) at 25° C./80% RH was 0.673%, which is slightly hygroscopic.

Example 12 High-Temperature Stability Test of the Crystal Form A of the Compound of Formula (I)

According to the "Guidelines for the Stability Test of Active Pharmaceutical Ingredients and Pharmaceutical Preparations" (Chinese Pharmacopoeia 2010 Appendix XIXC), the stability of the crystal form A of the compound of formula (I) under conditions of accelerated test at high temperature (60° C.) was investigated.

The crystal form A of the compound of formula (I) was placed in an open clean container at 60° C., and samples were taken on the 30th, 60th and 90th days respectively for testing. Comparing with the initial test results on day 0, the test results are shown in Table 4 below.

TABLE 4

Crystallization high-temperature stability test of the compound of formula (I)

| Sampling time (days) | Appearance | Content (%) | Total impurities (%) | Study on crystal form |
| --- | --- | --- | --- | --- |
| 0 | Off-white powder | 99.0 | 0.57 | Crystal form A |
| 30 | Off-white powder | 97.5 | 0.56 | Crystal form A |
| 60 | Off-white powder | 100.0 | 0.58 | Crystal form A |
| 90 | Off-white powder | 99.9 | 0.55 | Crystal form A |

Conclusion: The high-temperature stability test shows that crystal form A of the compound of formula (I) has good stability under high temperature conditions.

Example 13 High-Humidity Stability Test of the Crystal Form A of the Compound of Formula (I)

According to the "Guidelines for the Stability Test of Active Pharmaceutical Ingredients and Pharmaceutical Preparations" (Chinese Pharmacopoeia 2010 Appendix XIXC), the stability of the crystal form A of the compound of formula (I) under conditions of accelerated test at high humidity (40° C./75% humidity (open)) was investigated.

The crystal form A of the compound of formula (I) was placed in a open container with constant temperature and humidity for accelerated test, with the conditions of 40° C./75% humidity (open), and samples were taken on the 30th, 60th and 90th days for testing. Comparing with the initial test results on day 0, the test results are shown in Table 5 below:

TABLE 5

Crystallization high-humidity stability test of the compound of formula (I)

| Test conditions | Sampling time (days) | Appearance | Content (%) | Total impurities (%) | Study on crystal form |
| --- | --- | --- | --- | --- | --- |
| 40° C./75% humidity (open) | 0 | Off-white powder | 99.0 | 0.57 | Crystal form A |
| | 30 | Off-white powder | 100.6 | 0.57 | Crystal form A |
| | 60 | Off-white powder | 101.1 | 0.58 | Crystal form A |
| | 90 | Off-white powder | 100.4 | 0.58 | Crystal form A |

Conclusion: The high-humidity stability test shows that the crystal form A of the compound of formula (I) has good stability under high humidity conditions.

What is claimed is:

1. A crystal form A of a compound of formula (I), characterized in that the X-ray powder diffraction pattern thereof has characteristic diffraction peaks at the following 2θ angles: 11.894°±0.2°, 17.502°±0.2°, 19.785°±0.2°, 24.072°±0.2° and 24.664°±0.2°

(I)

2. The crystal form A of claim 1, characterized in that the X-ray powder diffraction pattern thereof has characteristic diffraction peaks at the following 2θ angles: 9.553°±0.2°, 11.894°±0.2°, 15.370°±0.2°, 17.502°±0.2°, 19.785°±0.2°, 20.283°±0.2°, 24.072°±0.2° and 24.664°±0.2°.

3. The crystal form A of claim 2, characterized in that the X-ray powder diffraction pattern thereof is as shown in FIG. 1.

4. The crystal form A of claim 1, characterized in that the differential scanning calorimetry pattern thereof has an endothermic peak at 271.79° C.±3° C.

5. The crystal form A of claim 4, characterized in that the differential scanning calorimetry pattern thereof is as shown in FIG. 2.

6. The crystal form A of claim 1, characterized in that the thermogravimetric analysis pattern thereof shows 0.1075% of weight loss at 110.82° C.±3° C. and 1.105% of weight loss at 229.08° C.±3° C.

7. The crystal form A of claim 6, characterized in that the thermogravimetric analysis pattern thereof is as shown in FIG. 3.

8. A crystal form B of a compound of formula (II), characterized in that the X-ray powder diffraction pattern thereof has characteristic diffraction peaks at the following 2θ angles: 13.349±0.2°, 19.012±0.2°, 20.235±0.2° and 23.370±0.2, (II)

9. The crystal form B of claim 8, characterized in that the X-ray powder diffraction pattern thereof has characteristic diffraction peaks at the following 2θ angles: 13.349±0.2°, 15.066±0.2°, 16.782±0.2°, 19.012±0.2°, 20.235±0.2°, 22.027±0.2°, 23.370±0.2° and 27.253±0.2°.

10. The crystal form B of claim 9, characterized in that the X-ray powder diffraction pattern thereof is as shown in FIG. 4.

11. The crystal form B of claim 8, characterized in that the differential scanning calorimetry pattern thereof has an endothermic peak at 234.43° C.±3° C.

12. The crystal form B of claim 11, characterized in that the differential scanning calorimetry pattern thereof is as shown in FIG. 5.

13. The crystal form B of claim 8, characterized in that the thermogravimetric analysis pattern thereof shows 0.3043% of weight loss at 120° C.±3° C. and 1.599% of weight loss at 238.46° C.±3° C.

14. The crystal form B of claim 13, characterized in that the thermogravimetric analysis pattern thereof is as shown in FIG. 6.

15. A method for treating cancers demonstrated to be directly or indirectly associated with TGF-βRI signaling in a subject in need thereof, comprising administering an effective amount of the crystal form A of claim 1 to the subject.

16. A method for treating cancers demonstrated to be directly or indirectly associated with TGF-βRI signaling in a subject in need thereof, comprising administering an effective amount of the crystal form B of claim 8 to the subject.

* * * * *